(12) United States Patent
Furusawa

(10) Patent No.: US 6,175,005 B1
(45) Date of Patent: Jan. 16, 2001

(54) PROCESS FOR THE PREPARATION OF CYCLIC ETHERS CONTAINING AN O-SILYLATED HYDROXYL GROUP

(75) Inventor: Kiyotaka Furusawa, Tsukuba (JP)

(73) Assignee: Director-General of Agency of Industrial Science and Technology (JP)

( * ) Notice: Under 35 U.S.C. 154(b), the term of this patent shall be extended for 0 days.

(21) Appl. No.: 09/271,165

(22) Filed: Mar. 18, 1999

(30) Foreign Application Priority Data

Aug. 7, 1998 (JP) .................................................. 10-224979

(51) Int. Cl.$^7$ .................................................. C07H 19/04
(52) U.S. Cl. .................................. 536/25.31; 536/27.11; 536/124
(58) Field of Search ................................. 536/27.11, 124, 536/25.31

(56) References Cited

U.S. PATENT DOCUMENTS

| | | | |
|---|---|---|---|
| 5,552,534 | * | 9/1996 | Hirschmann et al. ............... 536/17.4 |
| 5,892,008 | * | 4/1999 | Ku et al. .............................. 536/18.5 |

OTHER PUBLICATIONS

Jones et al., "Migration of t–Butyldimethylsilyl Protecting Grouops," *Journal of the Chemical Society, Perkin Transactions I*, 1979, 2762–2764.*
Gundlach et al., "Synthesis of Guanosine Analogs Bearing Pendant Alkylthiol Tethers," *Tetrahedron Letters*, 33(23), 4039–4042 (Jun. 9, 1997).*
Wada et al., "Regioselective Protection of the 2'–Hydroxyl Group of N–Acyl–3', 5'–O–di(t–butyl)silanediylnucleosie Derivatives by Use of t–BuMgCl and 2–(Trimethylsilyl)ethoxymethyl Chloride," *Tetrahedron Letters*, 36(10), 1683–1684 (Mar. 6, 1995).*
Trost et al., "The Di–t–Butylsilylene Protecting Group for Diols," *Tetrahedron Letters*, 22(50), 4999–5002 (1981).*
Furasawa, "Removal of Cyclic Di–t–butylsilanediyl Protecting Groups Using Tributylamine Hydrofluoride (TBAHF) Reagent," *Chemistry Letters*, (Issue No. 3), 509–510 (Mar. 1989).*
Aldrich Chemical Company, "Catalog Handbook of Fine Chemicals," Milwaukee, WI, 1994–1995, only p. 459 supplied, see especially the compound numbered 26,202–1.*
Corey et al., "Diisopropylsilyl Ditriflate and Di–tert–butylsilyl Ditriflate: New Reagents for the Protection of Diols," *Tetrahedron Letters*, 23(47), 4871–4874 (1982).*

Sekine et al., "Synthesis of a New Class of 2'–Phosphorylated Oligonucleotides Capable of Conversionto Oligonucleotides," *Journal of Organic Chemistry*, 58(11), 3204–3208 (May 21, 1993).*
Furusawa et al., "Synthesis and Restricted Conformation of 3', 5'–O–(Di–t–butylsilanediyl)ribonucleosides," *Chemistry Letters*, 1990, (Issue No. 1), pp. 97–100 (Jan. 1990).*
Ohtsuka et al., "Chemical Synthesis of RNA," Chapter 5 in *Synthesis and Applications of DNA and RNA*, Narang (ed.), Academic Press, Inc., New York, NY, 1987, only title and text pp. 115–136 supplied.*
Furusawa et al., "Synthesis of N–Protected Deoxynuleosides Via 3', 5'–Cyclic Silyl Derivatives," *Eleventh Symposium on Nucleic Acids Chemistry*, Tokyo, Japan, Nov. 1–2, 1983, published in *Nucleic Acids Research Symposium Series*, No. 12, Pritchard (ed.), IRL Press, Ltd., Washington, DC, 1983, only title and text pp. 21–23 supplied.*
Furuta et al., "Enhanced Transport of Nucleoside and Nucleotide Analogs with Complementary Base–Pairing Agents," *Journal of the American Chemical Society*, 113(21), 4706–4707 (Jun. 5, 1991).*
Wu et al., "A Study on the Alkylsilyl Groups in Oligoribonucleotide Synthesis," *Journal of Organic Chemistry*, 55(15), 4717–4724 (Jul. 20, 1990).*

* cited by examiner

*Primary Examiner*—Gary Geist
*Assistant Examiner*—L E Crane
(74) *Attorney, Agent, or Firm*—Lorusso & Loud

(57) ABSTRACT

A process is provided which can easily produce a hydroxyl groups-containing cyclic ether compound in which at least one of the hydroxyl groups except a primary hydroxyl group thereof and its neighboring secondary hydroxyl group is protected. A hydroxyl groups-containing cyclic ether is reacted with a difunctional silicon compound represented by the following formula (2)

$$R^2R^3SiX^1{}_2 \qquad (2)$$

wherein $R^2$ and $R^3$ each represent an aromatic group or a branched aliphatic group having at least 3 carbon atoms and $X^1$ represents a residue of an acid, then with a monofunctional silicon compound represented by the following formula (3)

$$R^4R^5R^6SiX^2 \qquad (3)$$

wherein $R^4$, $R^5$ and $R^6$ each represent an aromatic group or an aliphatic group and $X_2$ represents an eliminative group, and then with hydrofluoric acid in the presence of a base.

9 Claims, No Drawings

PROCESS FOR THE PREPARATION OF CYCLIC ETHERS CONTAINING AN O-SILYLATED HYDROXYL GROUP

BACKGROUND OF THE INVENTION

1. Field of the Invention

This invention relates to a process for the preparation of a cyclic ether containing an O-silylated hydroxyl group.

2. Prior Art

Recent widespread development of genetic engineering attracts people's attention to various kinds of nucleic acid derivatives as functional substances or pharmaceuticals. Thus, intensive studies are being made on derivatives of nucleosides constituting a basic skeleton of nucleic acids, as starting or intermediate materials for the production of nucleic acid derivatives. Technology developed up to date is primarily concerned with deoxyribonucleic acids. Whilst a deoxyribonucleoside contains a primary hydroxyl group and a secondary hydroxyl group in its molecule, a ribonucleoside in ribonucleic acids, which is now increasingly utilized, has three hydroxyl groups including one primary hydroxyl group and two secondary hydroxyl groups. Thus, as a starting material for the synthesis of RNA, a compound having its 2'-hydroxyl group previously protected similar to a deoxyribonucleoside is suited. A 2'-O-silylated ribonucleoside, which is important among others, has been hitherto prepared by a method in which a compound having its highly reactive primary hydroxyl group protected is first prepared. The other two hydroxyl groups are silylated and the product is separated by chromatography. With this method, however, it is difficult to improve selectivity so that the desired compound is only obtained by toublesome treatments.

Similar to the ribonucleoside, an aldopyranose compound has one primary hydroxyl group and a plurality of secondary hydroxyl groups. When only the primary hydroxyl group at its 6-position and the secondary hydroxyl group at its 4-position are to participate a reaction, it is desired that the other reactive hydroxyl groups be protected. However, there is no method which can easily introduce a protective group to the hydroxyl groups other than those at 4- and 6-positions.

SUMMARY OF THE INVENTION

It is an object of the present invention to provide a process which can easily produce a hydroxyl groups-containing cyclic ether compound in which at least one of the hydroxyl groups except a primary hydroxyl group thereof and its neighboring secondary hydroxyl group is protected.

In accordance with the present invention there is provided a process for the preparation of an 0-silylated hydroxyl group-containing cyclic ether represented by the following formula (4)

$$HOCH_2-CH-O-CH-R^1 \qquad (4)$$
$$| \qquad (Y^1)_t \qquad |$$
$$HO-CH-(Y^2)_q-CH-OSiR^4R^5R^6$$

wherein $R^1$ represents a substituent which does not react with a hereinafter described difunctional silicon compound, $Y^1$ and $Y^2$ each represent a methylene group, a hydroxymethylene group or a methylene group having a substituent which does not react with a hereinafter described difunctional silicon compound, t and q are each a number of 0 or 1, and $R^4$, $R^5$ and $R^6$ each represent an aromatic group or an aliphatic group, provided that, when $Y^1$ and $Y^2$ each represent a hydroxymethylene group, the hydroxyl group thereof is converted into $OSiR^4R^5R^6$ where $R^4$, $R^5$ and $R^6$ have the same meaning as above, characterized in that a hydroxyl groups-containing cyclic ether represented by the following formula (1)

$$HOCH_2-CH-O-CH-R^1 \qquad (1)$$
$$| \qquad (Y^1)_t \qquad |$$
$$HO-CH_2-(Y^2)_q-CH-OH$$

wherein $R^1$, $Y^1$, $Y^2$, t and q have the same meaning as above, is reacted with the difunctional silicon compound represented by the following formula (2)

$$R^2R^3SiX^1_2 \qquad (2)$$

wherein $R^2$ and $R^3$ each represent an aromatic group or a branched aliphatic group having at least 3 carbon atoms and $X^1$ represents a residue of an acid, then with a monofunctional silicon compound represented by the following formula (3)

$$R^4R^5R^6SiX^2 \qquad (3)$$

wherein $R^4$, $R^5$ and $R^6$ have the same meaning as above and $X^2$ represents an eliminative group, and then with hydrofluoric acid in the presence of a base.

The present invention also provides a process for the preparation of a 2'-O-silylated ribonucleoside represented by the following formula (6)

<chemical structure (6): furanose ring with HO, B, 2', HO, OSiR⁴R⁵R⁶> wherein B represents an unprotected or protected nucleic acid base and $R^4$, $R^5$ and $R^6$ each represent an aromatic group or an aliphatic group, characterized in that a ribonucleoside represented by the following formula (5)

<chemical structure (5): furanose ring with HO, B, HO, OH> wherein B has the same meaning as above,
is reacted with a difunctional silicon compound represented by the following formula (2)

$$R^2R^3SiX^1_2 \qquad (2)$$

wherein $R^2$ and $R^3$ each represent an aromatic group or a branched aliphatic group having at least 3 carbon atoms and $X^1$ represents a residue of an acid, then with a monofunctional silicon compound represented by the following formula (3)

$$R^4R^5R^6SiX^2 \qquad (3)$$

wherein $R^4$, $R^5$ and $R^6$ each represent an aromatic group or an aliphatic group and $X^2$ represents an eliminative group, and then with hydrofluoric acid in the presence of a base.

The present invention further provides a process for the preparation of an O-silylated aldopyranose compound represented by the following formula (8)

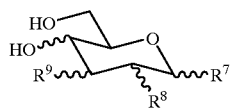

(8)

wherein $R^7$ represents a substituent which does not react with a hereinafter described difunctional silicon compound, at least one of $R^8$ and $R^9$ represents $OSiR^4R^5R^6$ (where $R^4$, $R^5$ and $R^6$ each represent an aromatic group or an aliphatic group) with the proviso that, when one of $R^8$ and $R^9$ does not represent $OSiR^4R^5R^6$, that $R^8$ or $R^9$ represents a substituent which does not react with a hereinafter described difunctional silicon compound, characterized in that a hydroxyl groups-containing cyclic ether represented by the following formula (7)

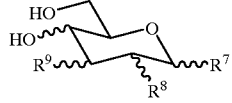

(7)

wherein $R^7$ has the same meaning as above, $R^8$ and $R^9$ each represent a hydroxyl group or a substituent which does not react with a hereinafter described difunctional silicon compound, with the proviso that at least one of $R^8$ and $R^9$ represents a hydroxyl group, is reacted with the difunctional silicon compound represented by the following formula (2)

$$R^2R^3SiX^1_2 \qquad (2)$$

wherein $R^2$ and $R^3$ each represent an aromatic group or a branched aliphatic group having at least 3 carbon atoms and $X^1$ represents a residue of an acid, then with a monofunctional silicon compound represented by the following formula (3)

$$R^4R^5R^6SiX^2 \qquad (3)$$

wherein $R^4$, $R^5$ and $R^6$ have the same meaning as above and $X^2$ represents an eliminative group, and then with hydrofluoric acid in the presence of a base.

Other objects, features and advantages of the present invention will become apparent from the detailed description of the preferred embodiments to follow.

DETAILED DESCRIPTION OF THE PREFERRED EMBODIMENTS OF THE INVENTION

The hydroxyl groups-containing cyclic ether represented by the general formula (1) includes ribonucleoside and aldopyranose compounds.

In the general formula (1), $R^1$ is a substituent which is not reactive with a difunctional silicon compound of the general formula (2). Such substituents include protected or unprotected nucleic acid bases, sugar compound residues, alkyl groups, alkoxy groups, substituted amino groups, substituted mercapto groups, acyl groups, acyloxy groups and various other groups and are suitably selected according to the desired compound.

In the general formula (1), $Y^1$ and $Y^2$ each represent a methylene group ($CH_2$), a hydroxymethylene group (CHOH) or a substituent which does not react with the above-described difunctional silicon compound. The substituent which does not react with the above-described difunctional silicon compound may be various groups as described above.

The symbols t and q each represent a number of 0 or 1. When t and q are 0, $(Y^1)t$ and $(y^2)q$ each represent a direct bond. When t and q are 1, the two carbon atoms adjacent each of $Y^1$ and $Y^2$ are bonded to each other through $Y^1$ and $Y^2$.

In the case of a ribonucleoside expressed by the general formula (5), the substituent B is a substituent which does not react with the above-described difunctional silicon compound. Examples of such substituents include unprotected or protected nucleic acid bases comprising a pyrimidine base and a purine base. The glycoside bond by which B and a sugar are bonded to each other may be of a β-type or an α-type. The protecting group is to protect a functional group, such as an amino group, an amide group or a hydroxyl group, of the nucleic acid base and may be any customarily employed group. For example, an acyl group, such as a benzoyl group, an isobutylyl group or a phenoxyacetyl group, may be used for protecting an amino group or an amide group. For the protection of an hydroxyl group, an arylalkyl group such as a benzyl group or a phenethyl group may be used.

Illustrative of nucleic acid bases are adenine, guanine, cytosine, uracil, thymine, hypoxanthine, xanthine and pseudouracil. Illustrative of ribonucleoside of the general formula (5) are uridine, adenosine, cytidine, guanosine, inosine, xanthosine, pseudouridine, N-benzoyl derivatives thereof, N-isobutylyl derivatives thereof and phenoxyacetyl derivatives thereof.

In the general formula (7) for the aldopyranose compound, $R^7$ stands for a substituent which does not react with the above-described difunctional silicon compound and may be, for example, an alkoxy group, an aromatic oxy group, an acyloxy group, a substituted amino group, a substituted mercapto group or a sugar residue. The alkyl group for the alkoxy group may be an alkyl group having 1–20 carbon atoms, preferably 1–6 carbon atoms, more preferably 1–4 carbon atoms. The aromatic group for the aromatic oxy group may be an aryl group or an arylalkyl group. The acyl group may be one which has the above-described alkyl group having 1–20 carbon atoms, preferably 1–6 carbon atoms, more preferably 1–4 carbon atoms, or which has an aryl group. The substituent for the substituted amino group and substituted mercapto group may be, for example, an alkyl group, an aryl group or an arylalkyl group. The alkyl group may be one which has 1–8 carbon atoms, preferably 1–4 carbon atoms, such as methyl, ethyl, propyl, butyl or cyclohexyl. The aryl group may be, for example, phenyl or tolyl. The arylalkyl group may be, for example, benzyl or phenetyl. The sugar residue may be one obtained by removing one hydroxyl group from a sugar compound. The sugar compound may be a sugar alcohol, a monosaccharide or an oligosaccharide. The monosaccharide may be, for example, glucose or fructose. The oligosaccharide may have a structure in which 2–5 monosaccharides, preferably 2–3 monosaccharides, are connected to each other. Illustrative of such oligosaccharides are sucrose, trehalose, gentiobiose and oligosaccharides obtained by hydrolysis of polysaccharides.

In the general formula (7), $R^8$ and $R^9$ each represent a hydroxyl group or a substituent which does not react with the above-described difunctional silicon compound, with the proviso that at least one of $R^8$ and $R^9$ represents a hydroxyl group. As the substituent which does not react with the above-described difunctional silicon compound, various groups described above may be used.

Examples of suitable aldopyranose compounds represented by the general formula (7) include alkylglycosides and arylglycosides of a monosaccharide, such as glucose, galactose, mannose or lactose, or an oligosaccharide, and 2-acetylamide derivatives of these glycosides.

In the general formula (2) representing the difunctional silicon compound used as a reaction raw material in the present invention, $R^2$ and $R^3$ each represent an aromatic group or a branched aliphatic group having at least 3 carbon atoms. The aromatic group may be, for example, an aryl group such as phenyl, tolyl or naphthyl, or an arylalkyl group such as benzyl or phenethyl. The branched aliphatic group having at least 3 carbon atoms may be an iso-, sec- or tert-aliphatic group and may be in a linear or cyclic form. The branched aliphatic group has 3–8 carbon atoms, preferably 3–4 carbon atoms. The upper limit of the number of carbon atoms thereof is about 12. Illustrative of such branched aliphatic groups are isopropyl, isobutyl, sec-butyl, tert-butyl, isopentyl, neopentyl, tert-pentyl, isohexyl, tert-hexyl, isooctyl, tert-octyl, 1,1,2-trimethylpropyl (thexyl) and cyclohexyl. The use of tert-butyl as the branched aliphatic group is preferred. The group $X^1$ stands for a residue of an acid which may be an inorganic acid or an organic acid, such as nitric acid, perchloric acid or trifluoromethanesulfonic acid.

In the general formula (3) representing a monofunctional silicon compound used as a reaction raw material in the present invention, $R^4$, $R^5$ and $R^6$ each represent an aromatic group or an aliphatic group. As the aromatic group, there may be mentioned phenyl, tolyl, naphthyl, benzyl and phenethyl. The aliphatic group may be linear or cyclic. The linear aliphatic group may be of a straight chain or branched chain. The aliphatic group has 1–8 carbon atoms, preferably 1–6 carbon atoms. The upper limit of the number of the carbon atoms is about 12. Illustrative of such aliphatic groups are methyl, ethyl, vinyl, propyl, isopropyl, propenyl, butyl, isobutyl, tert-butyl, pentyl, isopentyl, neopentyl, hexyl, isohexyl, cyclohexyl, cyclohexenyl, octyl, isooctyl, cyclooctyl and 1,1,2-trimethylpropyl. The group $X^2$ represents an eliminative group such as a residue of an acid. Examples of such eliminative groups include those exemplified in connection with the group $X^1$ and, additionally, imidazole, N-methyltrifluoroacetamide and 3-pentene-2-on.

In the production of 2'-O-silylated ribonucleoside represented by the general formula (6), the ribonucleoside represented by the general formula (5) is reacted with the difunctional silicon compound represented by the general formula (2) to cyclize and silylate the hydroxyl groups at the 3'- and 5'-positions and to obtain a cyclic silylated product represented by the general formula (9) shown below. The silylated product is then reacted with the monofunctional silicon compound represented by the general formula (3) to convert the hydroxyl group at 2'-position into $OSiR^4R^5R^6$ and to obtain a linear silylated product represented by the general formula (10) shown below. This is then reacted with hydrofluoric acid in the presence of a base to remove the difunctional silicon group. As the base, there may be mentioned a cyclic amine, such as pyridine, and a linear amine, such as tributylamine or triethylamine.

The above reactions are carried out at a temperature in the range of from –10° C. to 50° C., preferably from 10° C. to 30° C. The reaction pressure is not specifically limited. Ambient pressure is generally adopted.

The above reactions are preferably performed in an organic solvent. Any organic solvent may be used as long as it can dissolve or disperse the raw material ribonucleoside. A polar organic solvent such as dimethylformamide, dimethylsulfoxide, tetrahydrofuran or dioxane is preferably used.

The difunctional silicon compound represented by the general formula (2) is used in an amount of 0.9–2 moles, preferably 1.0–1.1 moles, per mole of the ribonucleoside of the general formula (5).

In performing the process of the present invention, it is possible to use, as the difunctional silicon compound, a product previously obtained outside the reaction system or a product produced in situ. The in situ production of the difunctional silicon compound may be done by reaction of a silver salt of an acid with a dialkyldichlorosilane.

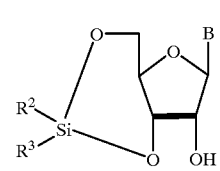

(9)

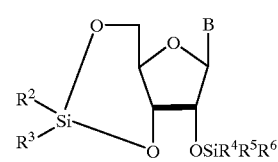

(10)

In the production of O-silylated aldopyranose represented by the general formula (8), the aldopyranose compound represented by the general formula (7) is reacted with the difunctional silicon compound represented by the general formula (2) to cyclize and silylate the hydroxyl groups at the 4- and 6-positions and to obtain a cyclic silylated product represented. The silylated product is then reacted with the monofunctional silicon compound represented by the general formula (3) to convert the hydroxyl groups other than those at 4- and 6-positions into $OSiR^4R^5R^6$. This is then reacted with hydrofluoric acid in the presence of a base to remove the difunctional silicon group. As the base, there may be mentioned a cyclic amine, such as pyridine, and a linear amine, such as tributylamine or triethylamine.

The above reactions are carried out at a temperature in the range of from –10° C. to 50° C., preferably from 10° C. to 30° C. The reaction pressure is not specifically limited. Ambient pressure is generally adopted.

The above reactions are preferably performed in an organic solvent. Any organic solvent may be used as long as it can dissolve or disperse the raw material sugar compound. A polar organic solvent such as dimethylformamide, dimethylsulfoxide, tetrahydrofuran or dioxane is preferably used.

The difunctional silicon compound represented by the general formula (2) is used in an amount of 0.9–2 moles, preferably 1.0–1.1 moles, per mole of the aldopyranose of the general formula (7).

In performing the process of the present invention, it is possible to use, as the difunctional silicon compound, a product previously obtained outside the reaction system or a product produced in situ. The in situ production of the difunctional silicon compound may be done by reaction of a silver salt of an acid with a dialkyldichlorosilane.

In the production of O-silylated aldopyranose compound using the aldopyranose compound as a raw material, when an aldopyranose compound having a hydroxyl group as a substituent $R^9$ at the 3-position is used as the raw material and is reacted with a difunctional silicon compound, a cyclic silylated product having a structure shown by the formula (11) below is obtained. When this substituted silyl compound is reacted with a monofunctional silicon compound, a silylated product having a structure shown by the formula (12) is obtained. The structure shown by the formula (13) below is a product obtained by removing the difunctional silicon compound from the silylated product.

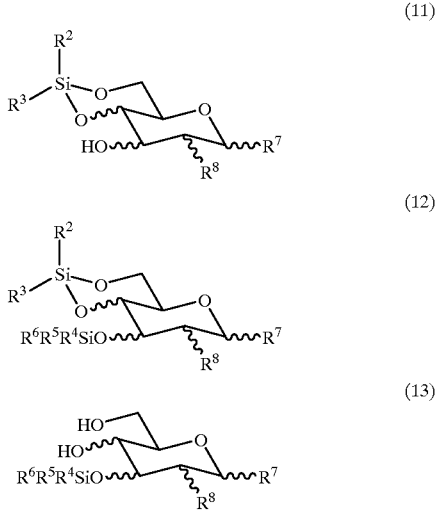

In the production of the O-silylated aldopyranose compound in the manner described above, when an aldopyranose compound having a hydroxyl group as a substituent $R^8$ at the 2-position is used, an O-silylated pyranose compound having $OSiR^4R^5R^6$ as $R^8$ is obtained. In a case where an aldopyranose compound in which both of the substituents $R^8$ and $R^9$ at 2- and 3-positions are hydroxyl groups is used, then an O-silylated pyranose compound in which both $R^8$ and $R^9$ are $OSiR^4R^5R^6$ is obtained.

The process of the O-silylated compound according to the present invention does not include troublesome procedures for the isolation of intermediate products and permits the whole reactions to be performed in one reactor by successively adding raw materials thereto. Thus, from a hydroxyl groups-containing cyclic ether such as a ribonucleoside or an aldopyranose as a starting compound, the end product can be synthesized in one stage. Thus, the end product can be easily prepared at low costs in accordance with the present invention.

EXAMPLES

The present invention will be further described in detail below by way of examples but should not be limited thereto.

Example 1

Uridine (0.5 mmol) was dissolved in 2 ml of N,N-dimethylformamide in anhydrous conditions in a reactor whose upper space was substituted by a dry nitrogen gas. Di-tert-butylsilylbis(trifluoromethanesulfonate) was then added in an equimolar amount and the mixture was reacted at room temperature for 4 minutes. The reaction was continued for 30 minutes after the addition of 6.5-fold mole of pyridine. Then, 1.05-fold mole of tert-butyldimethylsilyltrifluoromethanesulfonate was added and the reaction was performed for 2 hours. After addition of 12 ml of tetrahydrofuran, about 3-fold mole of hydrofluoric acid was added and the mixture was allowed to stand overnight. The reaction mixture was concentrated with an evaporator and the residues were subjected to a silica gel column chromatography to obtain 162 mg of a main product. The chromatographic behavior and instrumental analyses using proton NMR, etc. revealed that the product was the same as a sample whose structure was known and that the product was 2'-O-tert-butyldimethylsilyluridine.

Example 2

Adenosine (0.5 mmol) was dissolved in 3 ml of N,N-dimethylformamide in anhydrous conditions in a reactor whose upper space was substituted by a dry nitrogen gas. Di-tert-butylsilylbis(trifluoromethanesulfonate) was then added in an equimolar amount and the mixture was reacted at room temperature for 4 minutes. The reaction was continued for 30 minutes after the addition of 6.5-fold mole of pyridine. Then, 1.05-fold mole of tert-butyldimethylsilyltrifluoromethanesulfonate was added and the reaction was performed for 2 hours. After addition of 12 ml of tetrahydrofuran, about 3-fold mole of hydrofluoric acid was added and the mixture was allowed to stand overnight. The reaction mixture was concentrated with an evaporator and the residues were subjected to a silica gel column chromatography to obtain 171 mg of a main product. The proton NMR of the product gave peaks whose chemical shifts and peak areas were identical to those deduced from an intended structure. In addition, the two-dimensional NMR spectrum thereof showed that the tert-butyldimethylsilyl group was connected to the 2' hydroxyl group. Thus, the substance was confirmed to be 2'-O-tert-butyldimethylsilyladenosine.

Example 3

N-benzoyladenosine (0.5 mmol) was dissolved in 3 ml of N,N-dimethylformamide in anhydrous conditions in a reactor whose upper space was substituted by a dry nitrogen gas. Di-tert-butylsilylbis-(trifluoromethanesulfonate) was then added in an equimolar amount and the mixture was reacted at room temperature for 4 minutes. The reaction was continued for 30 minutes after the addition of 6.5-fold mole of pyridine. Then, 1.05-fold mole of tert-butyldimethylsilyltrifluoromethane-sulfonate was added and the reaction was performed for 2 hours. After addition of 12 ml of tetrahydrofuran, about 3-fold mole of hydrofluoric acid was added and the mixture was allowed to stand overnight. The reaction mixture was concentrated with an evaporator and the residues were subjected to a silica gel column chromatography to obtain 217 mg of a main product. The proton NMR of the product gave peaks whose chemical shifts and peak areas were identical to those deduced from an intended structure. In addition, the two-dimensional NMR spectrum thereof showed that the tert-butyldimethylsilyl group was connected to the 2'hydroxyl group. Thus, the substance was confirmed to be 2'-O-tert-butyldimethylsilyl-N-benzoyladenosine.

Example 4

N-benzoylsuanosine (0.5 mmol) was dissolved in 3 ml of N,N-dimethylformamide in anhydrous conditions in a reactor whose upper space was substituted by a dry nitrogen gas. Di-tert-butylsilylbis-(trifluoromethanesulfonate) was then added in an equimolar amount and the mixture was reacted at room temperature for 4 minutes. The reaction was continued for 30 minutes after the addition of 6.5-fold mole of pyridine. Then, 1.3-fold mole of tert-butyldimethylsilyltrifluoromethane-sulfonate was added and the reaction was performed for 2 hours. After addition of 12 ml of tetrahydrofuran, about 3-fold mole of hydrofluoric acid was added and the mixture was allowed to stand overnight. The reaction mixture was concentrated with an evaporator and the residues were subjected to a silica gel column chromatography to obtain 213 mg of a main product. The proton NMR of the product gave peaks whose chemical shifts and peak areas were identical to those deduced from an intended structure. In addition, the two-dimensional NMR spectrum thereof showed that the tert-butyldimethylsilyl group was connected to the 2'hydroxyl group. Thus, the substance was confirmed to be 2'-O-tert-butyldimethylsilyl-N-benzoylquanosine.

Example 5

Uridine (0.5 mmol) was dissolved in 3 ml of N,N-dimethylformamide in anhydrous conditions in a reactor whose upper space was substituted by a dry nitrogen gas. Di-tert-butylsilylbis(trifluoromethanesulfonate) was then added in an equimolar amount and the mixture was reacted at room temperature for 4 minutes. The reaction was continued for 30 minutes after the addition of 6.5-fold mole of pyridine. Then, 1.1-fold mole of dimethylthexylsilyltrifluoromethanesulfonate was added and the reaction was performed for 5 hours. After addition of 12 ml of tetrahydrofuran, about 3-fold mole of hydrofluoric acid was added and the mixture was allowed to stand overnight. The reaction mixture was concentrated with an evaporator and the residues were subjected to a silica gel column chromatography to obtain 150 mg of a main product. The proton NMR of the product gave peaks whose chemical shifts and peak areas were identical to those deduced from an intended structure. In addition, the two-dimensional NMR spectrum thereof showed that the dimethylthexylsilyl group was connected to the 2'hydroxyl group. Thus, the substance was confirmed to be 2'-O-dimethylthexylsilyluridine.

Example 6

Adenosine (0.5 mmol) was dissolved in 3 ml of N,N-dimethylformamide in anhydrous conditions in a reactor whose upper space was substituted by a dry nitrogen gas. Di-tert-butylsilylbis(trifluoromethanesulfonate) was then added in an equimolar amount and the mixture was reacted at room temperature for 4 minutes. The reaction was continued for 30 minutes after the addition of 6.5-fold mole of pyridine. Then, 1.1-fold mole of triisopropylsilyltrifluoromethanesulfonate was added and the reaction was performed for 12 hours. After addition of 12 ml of tetrahydrofuran, about 3-fold mole of hydrofluoric acid was added and the mixture was allowed to stand overnight. The reaction mixture was concentrated with an evaporator and the residues were subjected to a silica gel column chromatography to obtain 168 mg of a main product. The proton NMR of the product gave peaks whose chemical shifts and peak areas were identical to those deduced from an intended structure. In addition, the two-dimensional NMR spectrum thereof showed that the triisopropyllsilyl group was connected to the 2'hydroxyl group. Thus, the substance was confirmed to be 2' -0-triisopropylsilyladenosine.

Example 7

Phenyl-2-acetoamido-2-deoxy-glucopyranoside (0.5 mmol) was dissolved in 3 ml of N,N-dimethylformamide in anhydrous conditions in a reactor whose upper space was substituted by a dry nitrogen gas. Di-tert-butylsilylbis (trifluoromethanesulfonate) was then added in an equimolar amount and the mixture was reacted at room temperature for 4 minutes. The reaction was continued for 30 minutes after the addition of 6.5-fold mole of pyridine. Then, 1.05-fold mole of tert-butyldimethylsilyltri-fluoromethanesulfonate was added and the reaction was performed for 2 hours. After addition of 12 ml of tetrahydrofuran, about 3-fold mole of hydrofluoric acid was added and the mixture was allowed to stand overnight. The reaction mixture was concentrated with an evaporator and the residues were subjected to a silica gel column chromatography to obtain 140 mg of a main product. The chromatographic behavior and instrumental analyses using proton NMR, etc. revealed that the product was phenyl-2-acetamido-2-deoxy-3-O-tert-butyldimethylsilyl-glucopyranoside.

What is claimed is:

1. A single stage process for the preparation of an O-silylated hydroxyl group-containing cyclic ether represented by formula (4):

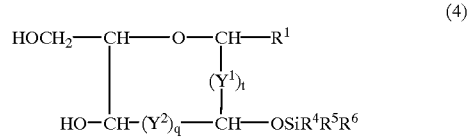

wherein $R^1$ represents a substituent which is unreactive with a hereinafter described difunctional silicon compound, $Y^1$ and $Y^2$ each represent a methylene group, a hydroxymethylene group or a methylene group having a substituent which is unreactive with a hereinafter described difunctional silicon compound, t and q are each a number of 0 or 1, and $R^4$, $R^5$ and $R^6$ each represent an aromatic group or an aliphatic group, provided that, when $Y^1$ and $Y^2$ each represent a hydroxymethylene group, the hydroxyl group thereof is converted into $OSiR^4R^5R^6$ where $R^4$, $R^5$ and $R^6$ have the same meaning as above, said process comprising:

reacting a hydroxyl groups-containing cyclic ether represented by formula (1):

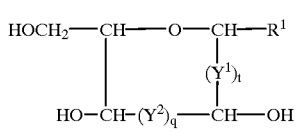

(1)

wherein $R^1$, $Y^1$, $Y^2$, t and q have the same meaning as above, with a difunctional silicon compound represented by formula (2):

$$R^2R^3SiX^1{}_2 \qquad (2)$$

wherein $R^2$ and $R^3$ each represent an aromatic group or a branched aliphatic group having at least 3 carbon atoms and $X^1$ represents a conjugate base of an acid, then with a monofunctional silicon compound represented by formula (3):

$$R^4R^5R^6SiX^2 \qquad (3)$$

wherein $R^4$, $R^5$ and $R^6$ have the same meaning as above and $X^2$ represents a leaving group, and then with hydrofluoric acid in the presence of a nitrogen base, said reactions of said cyclic ether with said difunctional silicon compound, with said monofunctional silicon compound and with said hydrofluoric acid being conducted in a single stage without isolation of any intermediate product.

2. A single stage process for the preparation of a 2'-O-silylated ribonucleoside represented by formula (6):

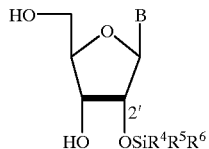

(6)

wherein B represents an unprotected or protected nucleic acid base and $R^4$, $R^5$ and $R^6$ each represent an aromatic group or an aliphatic group, said process comprising:

reacting a ribonucleoside represented by formula (5):

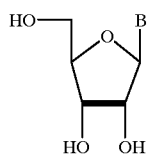

(5)

wherein B has the same meaning as above, with a difunctional silicon compound represented by formula (2):

$$R^2R^3SiX^1{}_2 \qquad (2)$$

wherein $R^2$ and $R^3$ each represent an aromatic group or a branched aliphatic group having at least 3 carbon atoms and $X^1$ represents a coniugate base of an acid, then with a monofunctional silicon compound represented by formula (3):

$$R^4R^5R^6SiX^2 \qquad (3)$$

wherein $R^4$, $R^5$ and $R^6$ each represent an aromatic group or an aliphatic group and $X^2$ represents a leaving group, and then with hydrofluoric acid in the presence of a nitrogen base, said reactions of said ribonucleoside with said difunctional silicon compound, with said monofunctional silicon compound and with said hydrofluoric acid being conducted in a single stage without isolation of any intermediate product.

3. A single stage process for the preparation of an O-silylated aldopyranose compound represented by formula (8):

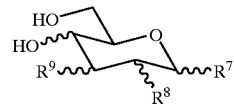

(8)

wherein $R^7$ represents a substituent which is unreactive with a hereinafter described difunctional silicon compound, at least one of $R^8$ and $R^9$ represents $OSiR^4R^5R^6$ (where $R^4$, $R^5$ and $R^6$ each represent an aromatic group or an aliphatic group) with the proviso that, when one of $R^8$ and $R^9$ does not represent $OSiR^4R^5R^6$, that $R^8$ or $R^9$ represents a substituent which is unreactive with a hereinafter described difunctional silicon compound, said process comprising:

reacting a hydroxyl groups-containing cyclic ether represented by formula (7):

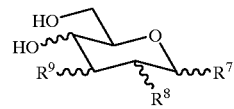

(7)

wherein $R^7$ has the same meaning as above, $R^8$ and $R^9$ each represent a hydroxyl group or a substituent which is unreactive with a hereinafter described difunctional silicon compound, with the proviso that at least one of $R^8$ and $R^9$ represents a hydroxyl group, with a difunctional silicon compound represented by formula (2):

$$R^2R^3SiX^1{}_2 \qquad (2)$$

wherein $R^2$ and $R^3$ each represent an aromatic group or a branched aliphatic group having at least 3 carbon atoms and $X^1$ represents a conjugate base of an acid, then with a monofunctional silicon compound represented by formula (3):

$$R^4R^5R^6SiX^2 \qquad (3)$$

wherein $R^4$, $R^5$ and $R^6$ have the same meaning as above and $X^2$ represents a leaving group, and then with hydrofluoric acid in the presence of a nitrogen base, said reactions of said silylated aldopyranose compound with said difunctional silicon compound, with said monofunctional silicon compound and with said hydrofluoric acid being conducted in a single stage without isolation of any intermediate product.

4. A process according to claim 1 wherein X' is a conjugate base of an acid selected from the group consisting of nitric acid, perchloric acid and trifluoromethanesulfonic acid.

5. A process according to claim 2 wherein X' is a conjugate base of an acid selected from the group consisting of nitric acid, perchloric acid and trifluoromethanesulfonic acid.

6. A process according to claim 3 wherein X' is a conjugate base of an acid selected from the group consisting of nitric acid, perchloric acid and trifluoromethanesulfonic acid.

7. A process according to claim 1 wherein q is 0.

8. A process according to claim 2 wherein q is 0.

9. A process according to claim 3 wherein q is 0.

* * * * *

UNITED STATES PATENT AND TRADEMARK OFFICE
CERTIFICATE OF CORRECTION

PATENT NO. : 6,175,005 B1
DATED : January 16, 2001
INVENTOR(S) : Furusawa

It is certified that error appears in the above-identified patent and that said Letters Patent is hereby corrected as shown below:

Title page,
OTHER PUBLICATIONS, line 8, "silanediylnucleosie" should read
-- silanediylnucleoside --.

ABSTRACT,
Line 11, "monofunction" should read -- monofunctional --;
Line 12, delete "al".

Column 4,
Line 23, "$(y^2)$" should read -- $(Y^2)$ --.

Column 8,
Line 65, "butyldimethylsilyltrifluoromethane-sulfonate" should read
-- butyldimethylsilyltrifluoromethanesulfonate --.

Column 9,
Line 22, "butyldimethylsilyltrifluoromethane-sulfonate" should read
-- butyldimethylsilyltrifluoromethanesulfonate --.

Column 10,
Line 29, "tert-butyldimethylsilyltri-fluoromethanesulfonate" should read
-- "tert-butyldimethylsilyltrifluoromethanesulfonate --.

Column 12,
Line 62, delete "silylated aldopy-"; and

Signed and Sealed this

Twenty-sixth Day of February, 2002

*Attest:*

*Attesting Officer*

JAMES E. ROGAN
*Director of the United States Patent and Trademark Office*